US012605513B2

(12) United States Patent
Kulkarni et al.

(10) Patent No.: US 12,605,513 B2
(45) Date of Patent: Apr. 21, 2026

(54) ADAPTOR FOR MOUNTING ONTO A MEDICAL CONTAINER, A MEDICAL CONTAINER COMPRISING SAID ADAPTOR, AND A METHOD FOR MANUFACTURING SAID ADAPTOR

(71) Applicant: Becton Dickinson France, Le Pont-de-Claix (FR)

(72) Inventors: Pooja Bhuvanesh Kulkarni, Pune (IN); Nicolas Euvrard, Plainsboro, NJ (US); Cédric Rivier, Voreppe (FR); Rajesh Poola, Chennai (IN); Julien Gagliano, Grenoble (FR); Frédéric Michel, Rives (FR)

(73) Assignee: Becton Dickinson France, Le Pont-de-Claix (FR)

( * ) Notice: Subject to any disclaimer, the term of this patent is extended or adjusted under 35 U.S.C. 154(b) by 815 days.

(21) Appl. No.: 17/800,257

(22) PCT Filed: Feb. 17, 2021

(86) PCT No.: PCT/EP2021/053850
§ 371 (c)(1),
(2) Date: Aug. 17, 2022

(87) PCT Pub. No.: WO2021/165296
PCT Pub. Date: Aug. 26, 2021

(65) Prior Publication Data
US 2023/0075695 A1 Mar. 9, 2023

(30) Foreign Application Priority Data
Feb. 18, 2020 (EP) ..................................... 20305152

(51) Int. Cl.
*A61M 5/34* (2006.01)
*A61M 39/10* (2006.01)

(52) U.S. Cl.
CPC ........ *A61M 5/345* (2013.01); *A61M 39/1011* (2013.01); *A61M 2039/1033* (2013.01); *A61M 2039/1077* (2013.01)

(58) Field of Classification Search
CPC .................. A61M 5/344; A61M 5/345; A61M 2039/1077; A61M 5/347
See application file for complete search history.

(56) References Cited

U.S. PATENT DOCUMENTS 5,851,201 A * 12/1998 Ritger ................... A61M 39/10
604/533
9,234,616 B2 1/2016 Carrez et al.
(Continued)

FOREIGN PATENT DOCUMENTS

CN 104288855 A 1/2015
CN 110461406 A 11/2019
(Continued)

*Primary Examiner* — Kami A Bosworth
(74) *Attorney, Agent, or Firm* — The Webb Law Firm

(57) ABSTRACT

An adaptor for mounting onto a medical container, the adaptor including a distal part configured to receive a connector, and a proximal part configured to be mounted onto the distal tip of the medical container. The proximal part includes an inner ring protruding from a lateral tubular wall of the adaptor, said inner ring having an inner edge that delimits an opening configured to receive the distal tip. The proximal part further includes a gripping member made of an elastomer material, said gripping member being connected to the inner edge of the inner ring in order to be in contact with an outer surface of the distal tip when the adaptor is mounted onto the medical container.

8 Claims, 5 Drawing Sheets

(56)                    References Cited

U.S. PATENT DOCUMENTS

|  |  |  |  |
|---|---|---|---|
| 9,717,855 B2 | 8/2017 | Bosshardt et al. | |
| 10,258,540 B2 | 4/2019 | Poncon et al. | |
| 11,135,417 B2 | 10/2021 | Yoshioka et al. | |
| 11,833,339 B2 | 12/2023 | Flippe et al. | |
| 2015/0246184 A1* | 9/2015 | Hund .................... | A61M 5/345 |
| | | | 604/240 |
| 2015/0283372 A1 | 10/2015 | Maritan et al. | |

FOREIGN PATENT DOCUMENTS

| | | | | |
|---|---|---|---|---|
| EP | 2826519 A1 | 1/2015 | | |
| EP | 3381503 A1 * | 10/2018 | ........ | A61M 39/1011 |
| JP | 2013252354 A | 12/2013 | | |
| JP | 2014502524 A | 2/2014 | | |
| JP | 2014528741 A | 10/2014 | | |
| JP | 2016525395 A | 8/2016 | | |
| JP | 2018519044 A | 7/2018 | | |
| WO | 2012049532 A1 | 4/2012 | | |
| WO | 2015007650 A1 | 1/2015 | | |
| WO | 2015156272 A1 | 10/2015 | | |
| WO | 2016198580 A1 | 12/2016 | | |

* cited by examiner

ADAPTOR FOR MOUNTING ONTO A MEDICAL CONTAINER, A MEDICAL CONTAINER COMPRISING SAID ADAPTOR, AND A METHOD FOR MANUFACTURING SAID ADAPTOR

CROSS-REFERENCE TO RELATED APPLICATIONS

This application is the United States national phase of International Application No. PCT/EP2021/053850 filed Feb. 17, 2021, and claims priority to European Patent Application No. 20305152.9 filed Feb. 18, 2020, the disclosures of which are hereby incorporated by reference in their entirety.

BACKGROUND OF THE DISCLOSURE

Field of the Disclosure

The present disclosure relates to an adaptor for mounting onto a medical container, a medical container comprising said adaptor, and a method for manufacturing said adaptor.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to an adaptor or a medical container of the invention, and the "proximal direction" is to be understood as meaning the opposite direction to said direction of injection, that is to say the direction towards the user's hand holding a medical container as for an injection operation.

Basically, medical containers, such as for example syringes, are preferably made of glass for its high chemical passivity, its low gas permeability and high transparency, which allows an extended storage and an easy inspection.

The medical containers usually comprise a barrel forming a reservoir for containing a medical product. The barrel has a distal end in the form of a longitudinal tip defining an axial passageway through which the medical product is expelled from the barrel. However, this longitudinal tip does not allow parenteral administration by itself and must either comprise a staked needle or an adaptor allowing the connection of the syringe to a connector such as a needle hub or an intravenous (IV) line.

Description of Related Art

It is important that the connection between the medical container and the adaptor is strong enough to prevent accidental disengagement, either during connection of the connector onto the adaptor, or caused by the fluid pressures within the medical container and connector.

The document WO2015/007650 discloses that adaptors may be secured around the longitudinal tip of the syringe by snap-fitting or friction force, for example by mechanical attaching means defined onto the longitudinal tip such as a groove or a ring. However, the incorporation of a groove to the longitudinal tip may cause the longitudinal tip to be sensitive to flaws and may potentially lead to tip breakage. Moreover, an adaptor connected around a longitudinal tip by snap-fitting or friction force may demonstrate both a limited torque and pull out force resistance. There is therefore a need for an adaptor that would improve the connection between the longitudinal tip of a medical container and said container. More specifically, there is a need for an adaptor that would improve the torque and the adaptor pull out force.

SUMMARY OF THE DISCLOSURE

An aspect of the disclosure is an adaptor for a medical container having a distal tip, said adaptor comprising a distal part configured to receive a connector, and a proximal part configured to be mounted onto the distal tip of the medical container, wherein the proximal part comprises an inner ring protruding from a lateral tubular wall of the adaptor, said inner ring having an inner edge that delimits an opening configured to receive the distal tip, and wherein the proximal part further comprises a gripping member made of an elastomer material, said gripping member being connected to the inner edge of the inner ring in order to be in contact with an outer surface of the distal tip when the adaptor is mounted onto the medical container.

The adaptor of the disclosure thus provides a higher grip between said adaptor and the distal tip of the medical container. The increased friction force exerted by the elastomer gripping member onto the distal tip improves the torque and increases the adaptor pull out force. Because the adaptor pull out force is increased there is less risk that the adaptor disconnects from the distal tip of the medical container. The elastomer material of the gripping member further reduces the risk that the adaptor rotates around the distal tip.

In an embodiment, the inner ring comprises a distal and a proximal abutment surface abutting against the gripping member in order to secure said elastomer gripping member in a longitudinal direction A of the adaptor.

This limits the risks of an axial disassembly between the elastomer gripping member and the inner ring.

In an embodiment, the inner ring comprises a protrusion or a recess, preferably a protrusion, that engages a complementarily shaped recess or protrusion, preferably a recess, provided on the elastomer gripping member in order to secure said elastomer gripping member to the inner ring.

Preferably, said protrusion or recess has a dovetail shape.

This limits the risks of an axial disassembly of the gripping member and the protruding ring due to an increased pull out force exerted on the adaptor.

In an embodiment, the elastomer gripping member comprises a free distal lip.

This improves the pull out force of the adaptor.

In an embodiment, the gripping member is over-molded or co-injection molded.

In an embodiment, the elastomer material of the gripping member is rubber or thermoplastic elastomer (TPE).

The inner ring may be made of acrylonitrile butadiene styrene (ABS). This improves the attachment of the elastomer gripping member to the inner ring.

In an embodiment, the gripping member is in the form of a 360° extending sleeve.

This provides a 360° grip between the adaptor and the medical container distal tip, thereby improving the torque and increasing the adaptor pull out force.

In an embodiment, the adaptor comprises several gripping members, each of said gripping members being in the form of a partial sleeve, the adjacent gripping members thereby delimiting gaps allowing the inner edge of the inner ring to be in contact with the outer surface of the distal tip when the adaptor is mounted onto the medical container.

Therefore, the inner edge of the inner ring and the elastomer gripping members alternately contact the distal tip in a circumferential direction. This prevents a tilting movement of the adaptor relative to the distal tip. A tilting movement is a rotation of the adaptor relative to said distal tip around an axis orthogonal to the longitudinal axis of the adaptor and the distal tip.

The inner edge may comprise radial protrusions extending through said gaps in order to radially abut against the distal tip. The radial protrusions thus extend between adjacent gripping members.

Another aspect of disclosure is a medical container comprising a distal tip and an adaptor having the above features.

In an embodiment, the distal tip comprises bumps configured to abut against the inner edge of the inner ring at the gaps delimited by the adjacent gripping members.

Another aspect of the disclosure is a method for manufacturing an adaptor as above-described, wherein the gripping member is overmolded or co-injection molded.

In an embodiment, the adaptor is formed in a two-shot injection molding.

BRIEF DESCRIPTION OF THE DRAWINGS

The disclosure and the advantages arising therefrom will clearly emerge from the detailed description that is given below with reference to the appended drawings as follows.

DETAILED DESCRIPTION

Figure 1:
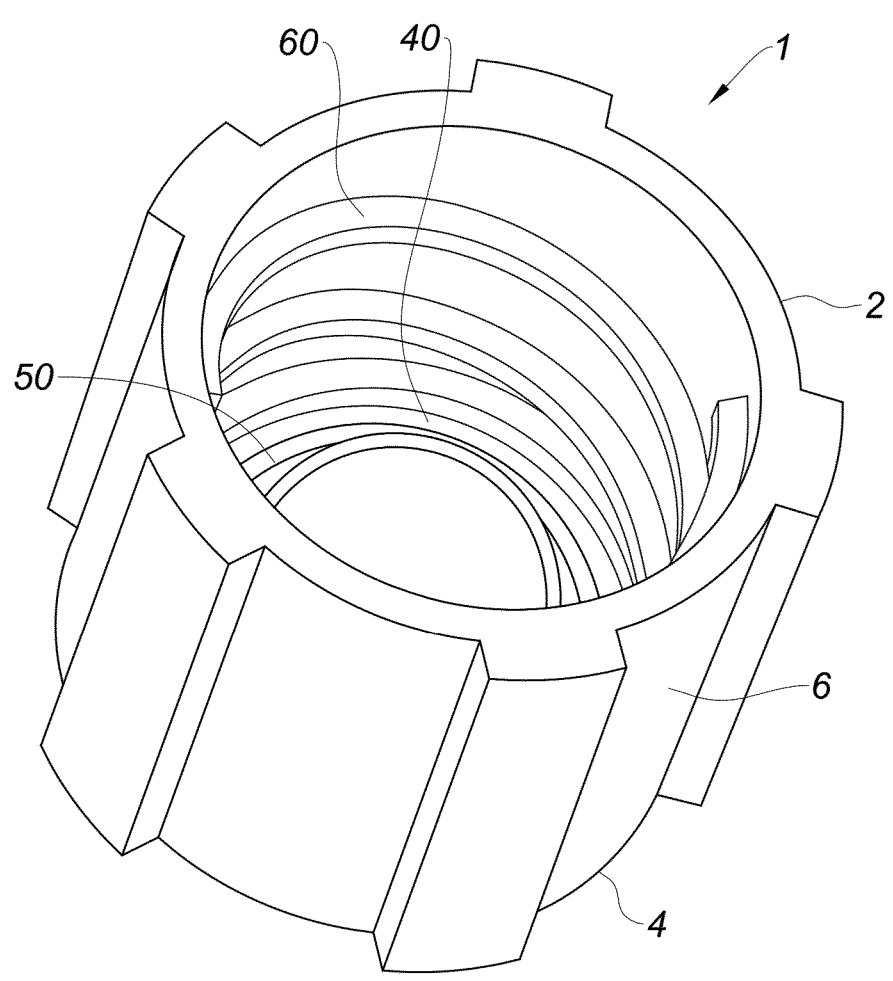
FIG. 1 is a perspective view of an adaptor according to an embodiment of the invention.
Figure 2:
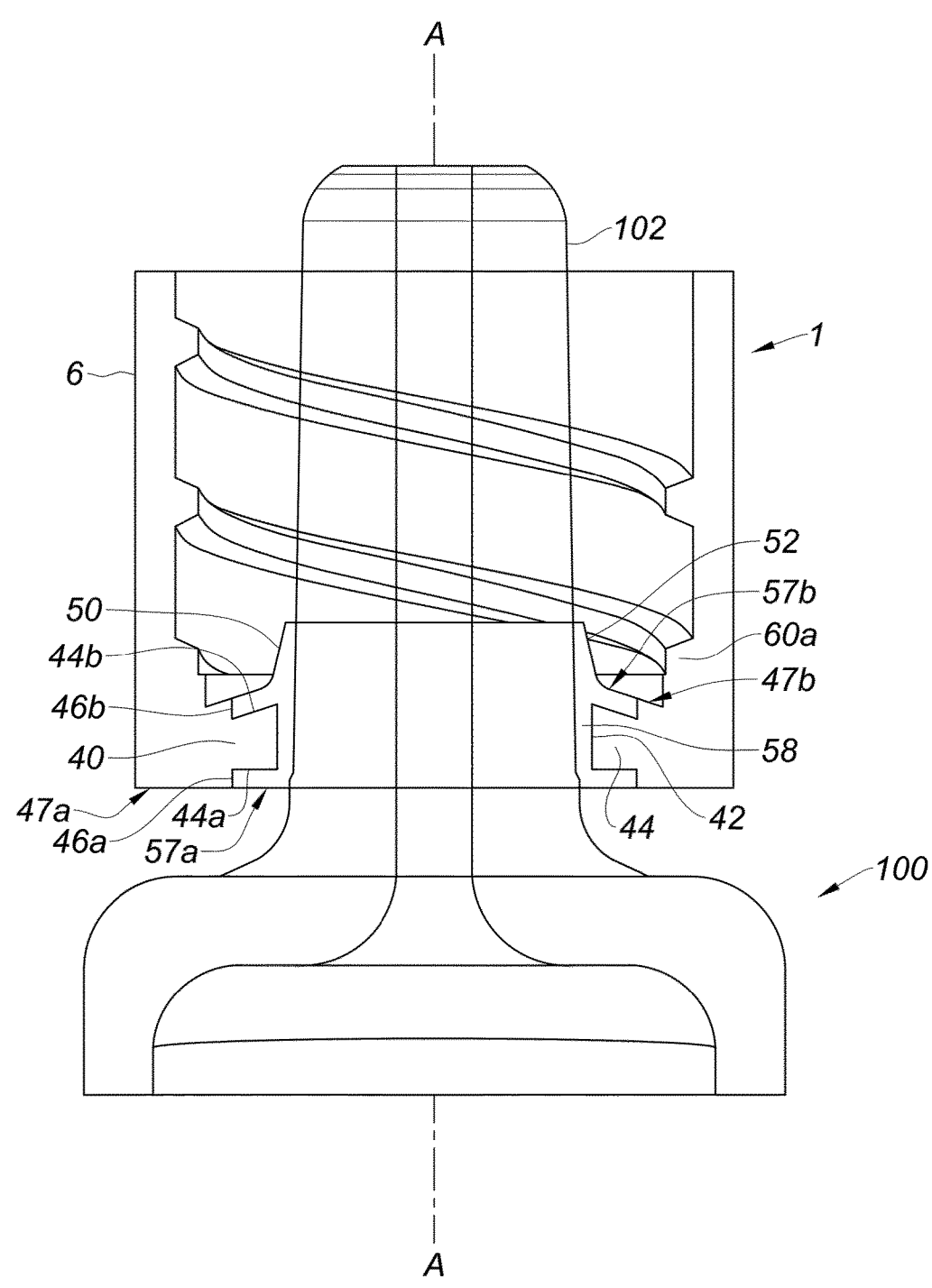
FIG. 2 is a longitudinal cross section view of an adaptor and a medical container according to an embodiment of the invention.
Figure 3:
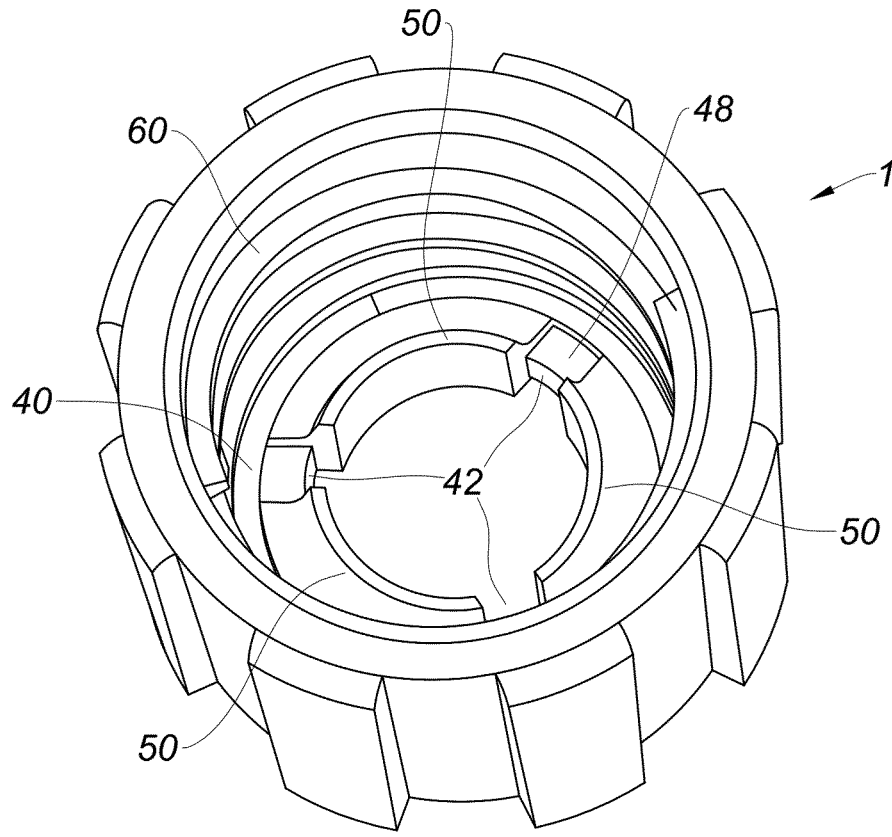
FIG. 3 is a perspective view of an adaptor according to an embodiment of the invention.
Figure 4:
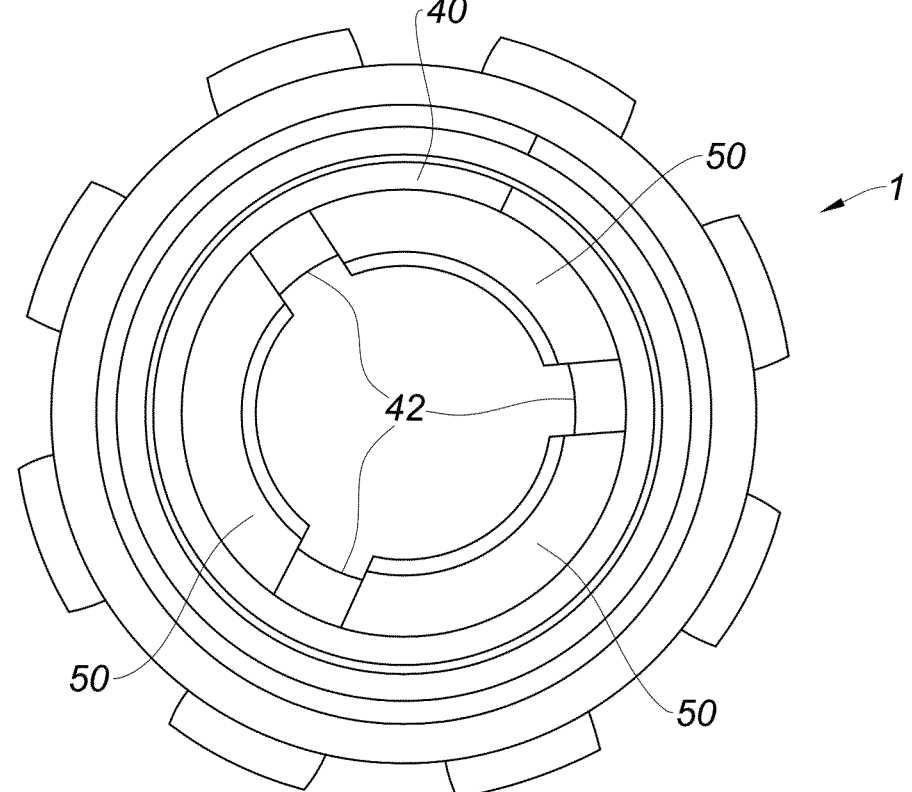
FIG. 4 is a top view of an adaptor according to an embodiment of the invention.

With reference to FIG. 1 is shown an adaptor 1 according to an embodiment of the disclosure. With reference to FIG. 2, the adaptor 1 is intended to be mounted onto a distal tip 102 of a medical container 100, more precisely onto an outer surface of said distal tip 102. The outer surface may be either cylindrical or distally tapered. The adaptor 1 permits to connect a connector, such as a needle hub or a syringe cap, to the medical container 100.

The adaptor 1 comprises a distal part 2 and a proximal part 4. The adaptor 1 comprises a tubular wall 6 defining an inner cavity around a central longitudinal axis A.

The distal part 2 is configured to receive the connector. As illustrated on FIG. 1, the distal part 2 defines a distal opening leading inside the inner cavity so as to receive the connector inside the adaptor 1. The distal part 2 includes connecting means, such as an internal thread 60, configured to engage corresponding connecting means, such as the wings of a needle hub or an external thread provided on a connector, in order to secure the connector to the adaptor 1 and accordingly to the medical container 100. The connecting means may alternatively comprise a bayonet element, a snapping element or a press-fit element.

The proximal part 4 is configured to secure the adaptor 1 to the distal tip 102 of the medical container 100. The proximal part 4 defines a proximal opening leading into the inner cavity so as to receive the distal tip 102 of the medical container 100 inside the adaptor 1. The proximal part 4 further comprises an inner ring 40 and at least one gripping member 50. The inner ring 40 and the gripping member 50 are configured to secure the adaptor 1 onto the distal tip 102 of the medical container 100.

The inner ring 40 inwardly and radially protrudes from the tubular wall 6 of the adaptor 1. The inner ring 40 is configured to support the gripping member 50. The gripping member 50 is thus connected to the rest of the adaptor 1 by means of inner ring 40 and preferably by means of this inner ring 40 only.

The inner ring 40 has an inner edge 42 defining the proximal opening. The inner edge 42 is configured to maintain said gripping member 50 against the outer surface of the distal tip 102 when the adaptor 1 is mounted onto the medical container 100. The gripping member 50 may thus be compressed by the outer surface against the inner edge 42 by the distal tip 102 having a frustoconical shape. The inner edge 42 may have a cylindrical shape and may preferably extend parallel to the longitudinal axis A. The inner edge 42 continuously extends in a circumferential direction.

The inner ring 40 preferably extends in a transversal plane that is orthogonal to the longitudinal axis A. Accordingly the inner ring 40 extends orthogonally to the tubular wall 6 of the adaptor 1. The inner ring 40 therefore better withstands deformation when the adaptor 1 is mounted onto the distal tip 102 and better maintains the gripping member 50 against the outer surface of the distal tip 102.

The inner ring 40, and more generally the rest of the adaptor 1 apart from the gripping member 50, may be made a plastic material, more precisely of any rigid polymer adapted to medical use, such as high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and combinations thereof. The rest of the adaptor 1 at least includes the inner ring 40 and may further include the proximal part 4, the tubular wall 6 and/or the distal part 2. Preferably, the adaptor 1, more specifically the inner ring 40, is made of acrylonitrile butadiene styrene (ABS). Furthermore, the adaptor 1 may preferably be made of a light-transmitting material.

The gripping member 50 is configured to secure the adaptor 1 to the distal tip 102. The gripping member 50 is made of a softer material than the inner ring 40 and more generally than the rest of the adaptor 1 in order to enhance the adherence of the proximal part of the adaptor 1 onto the distal tip 102. More specifically, the gripping member 50 is made of an elastomer material such as thermoplastic elastomer or rubber. The rubber may be either natural or synthetic rubber. The gripping member 50 thus forms an elastomer inner sleeve configured to secure the adaptor 1 to the medical container 100.

The gripping member 50 is supported by the inner ring 40. More specifically, the gripping member 50 covers the inner edge 42 of the inner ring 40. therefore, the gripping member 50 is configured to extend between said inner edge 42 and the distal tip 102 of the medical container 100. As shown on FIG. 2, the gripping member 50 advantageously stands remote from the tubular wall 6 or the internal thread 60 of the adaptor 1. The gripping member 50 may fully cover the inner edge 42.

The gripping member 50 is fixedly attached to the inner edge 42 of the inner ring 40. For example, the gripping member 50 may be over-molded or may be co-injection molded with the inner ring 40 and more generally with the rest of the adaptor 1. The inner ring 40 and the gripping member 50 thus form a single-piece adaptor 1 made of two different materials. By single-piece adaptor 1 it is meant that the inner ring 40 and the gripping member 50 that are made of different materials form together a single piece that cannot be disassembled or separated without damaging the adaptor 1. The gripping member 50 is thus fixed relative to the inner ring 40.

In order to prevent any sliding movement of the gripping member 50 relative to the inner ring 40, the inner ring 40 may comprise a proximal abutment surface 44a and a distal abutment surface 44b. The gripping member 50 is preferably secured to these proximal and distal abutment surfaces 44a, 44b.

Figure 5:
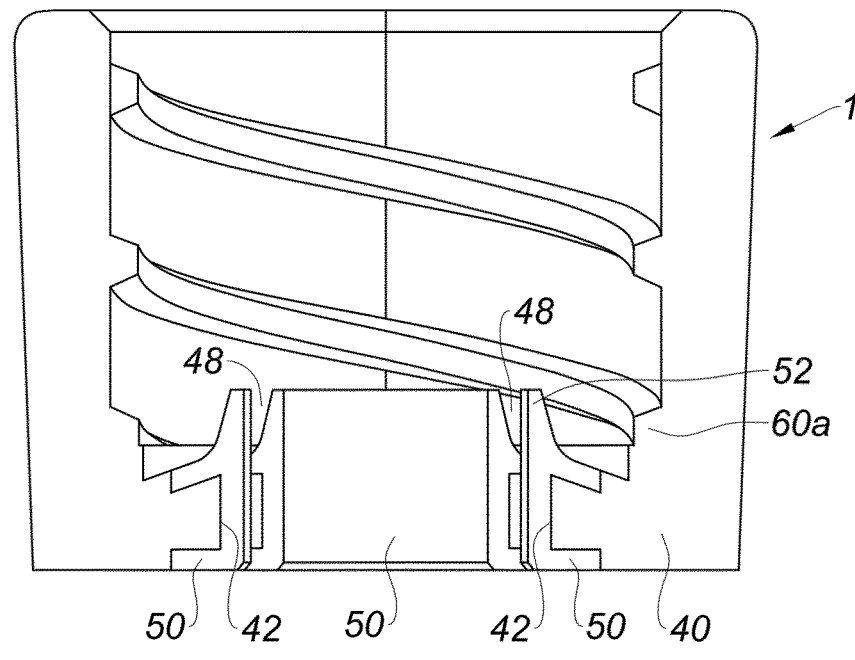
FIG. 5 is a longitudinal cross section view of an adaptor according to an embodiment of the invention.
Figure 6:
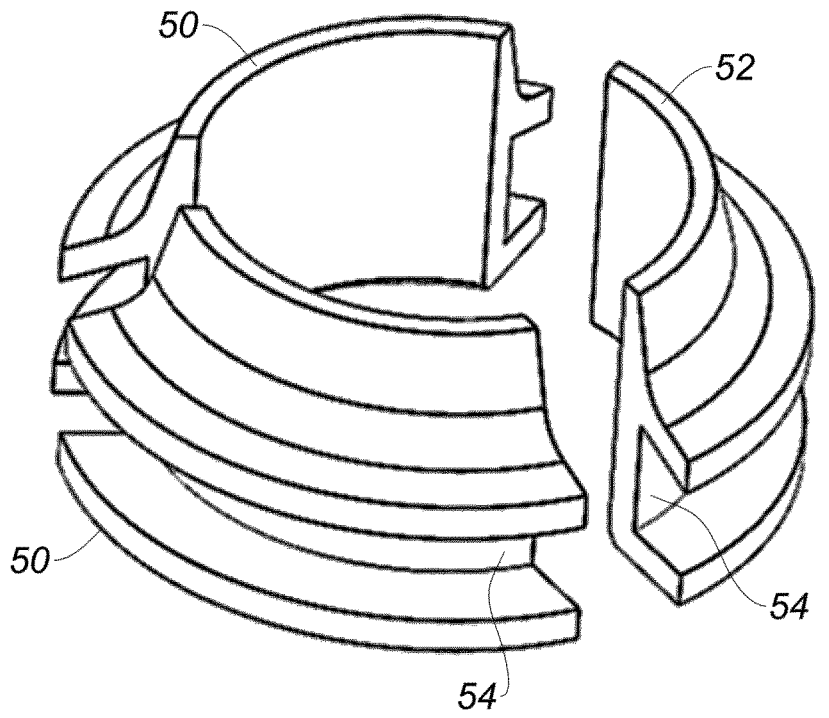
FIG. 6 is a perspective view of elastomer gripping members of an adaptor according to an embodiment of the invention.

As visible on FIG. 2, the proximal and the distal abutment surfaces 44a, 44b may be provided at the two lateral sides of a radial protrusion 44, such as a circular rib, provided on the inner ring 40. The gripping member 50 may define a complementarily shaped recess 54, as illustrated on FIG. 6, configured to receive the radial protrusion 44. The proximal and/or distal abutment surfaces 44a, 44b may be inclined relative to a transversal plane. Accordingly, and as visible on FIGS. 2 and 5, the radial protrusion 44 and the complementarily shaped recess 54 preferably form a dovetail joint in order to reduce risks that the gripping member 50 be removed. In an alternative embodiment not shown, the recess 54 may be provided on the inner ring 40, said recess being for example in the form of a circular groove, while said radial protrusion 44 may be provided on the gripping member 50. In this case, the proximal and the distal abutment surfaces 44a, 44b may be provided at the two lateral sides of the circular groove of the inner ring 40.

The inner ring 40 may further comprise a radial bottom shoulder 46a and/or a radial top shoulder 46b. The bottom and top shoulders 46a, 46b are respectively arranged proximally and distally relative to the inner edge 42. The gripping member 50 is advantageously also secured to the radial bottom shoulder 46a and/or top shoulder 46b.

It should also be noted that the gripping member 50 may have a bottom proximal face 57a that does not go beyond a bottom proximal face 47a of the inner ring 40. The gripping member 50 may also have a top distal face 57b that does not go beyond a top distal face 47b of the inner ring 40. Preferably, the bottom proximal face 57a of the gripping member 50 is flush with the bottom proximal face 47a of the inner ring 40, and/or the top distal face 57b of the gripping member 50 is flush with the top distal face 47b of the inner ring 40.

As shown on FIG. 2, the gripping member 50 advantageously comprises a free distal lip 52 that may extend parallel to the longitudinal axis A. The free distal lip 52 is configured to prevent any tilting movement of the adaptor 1 relative to the distal tip 102, i.e. any rotation of the adaptor 1 around a transversal axis, when the adaptor 1 is mounted onto the distal tip 102. A transversal axis is an axis that is othrogonal to the longitudinal axis A. The free distal lip 52 distally extends from a base portion 58 of the gripping member 50, said base portion 58 being secured to the inner ring 40. The free distal lip 52 may distally extend beyond a proximal end 60a of the internal thread 60. As visible on FIG. 2, the free distal lip 52 is advantageously distally tapered.

According to FIGS. 1 and 2, the adaptor 1 comprises a single gripping member 50. The gripping member 50 may be in the form of a 360° sleeve. In this embodiment, only the gripping member 50 of the adaptor 1 contacts the distal tip 102.

Alternatively, as shown on FIGS. 3 to 6, the gripping member 50 may be in the form of a circumferentially discontinued sleeve. The adaptor 1 actually comprises a plurality of gripping members 50, each in the form of a partial sleeve or cylinder. As illustrated on FIGS. 3 to 6, the adaptor 1 may comprise at least three gripping members 50 that are remote from each other. These gripping members 50 may be regularly distributed in a circumferential direction. As visible on FIGS. 3 and 4, the gripping members 50 are separated from each other by circumferential gaps 48 allowing the inner edge 42 of the inner ring 40 to contact the distal tip 102 of the medical container 100 when the adaptor 1 is mounted onto the distal tip 102 of said medical container 100. As a result, the inner edge 42 contacts the distal tip 102 in alternation with the gripping members 50 along a circumferential direction. This helps prevent a tilting movement of the adaptor 1 relative to the distal tip 102. Preferably, the gripping members 50 are longer than the gaps 48 in a circumferential direction. Although not shown on FIGS. 3-6, the inner edge 42 may include radial protrusions extending in the gaps 48, i.e. between adjacent gripping members 50, in order to contact the outer surface of the distal tip 102. Alternatively or complementarily, the distal tip 102 comprises radial bumps that are received in the gaps delimited by the gripping members 50, these radial bumps contacting the inner edge 42. This permits a rigid connection between the adaptor 1 and the distal tip 102.

Figure 7:
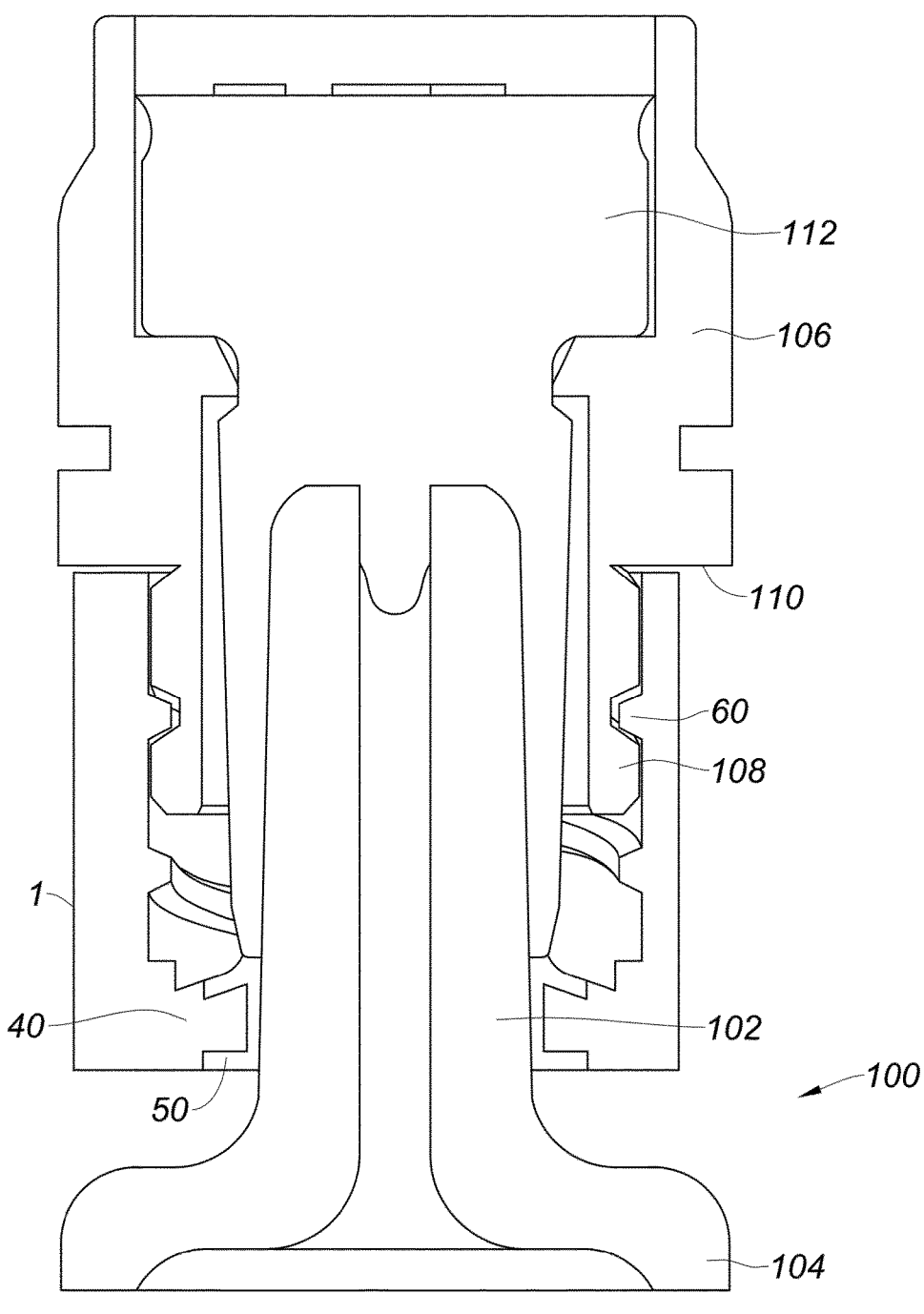
FIG. 7 is a cross section view of an adaptor and a medical container according to an embodiment of the invention.

The disclosure also relates to a medical container 100 as shown for example on FIG. 2 or 7. The medical container 100 may be a syringe, such as pre-fillable or prefilled syringe. The medical container 100 comprises a tubular barrel 104 that defines a reservoir for a medical product. The distal tip 102 may be cylindrical or distally tapered. The tubular barrel 104 and the distal tip 102 are preferably made of glass. The medical container 100 further comprises the above-described adaptor 1 that is secured onto the distal tip 102 by means of the gripping member 50 adhering to the outer surface of the distal tip 102. In order to improve the interference fit between the adaptor 1 and the gripping member 50 the gripping member 50 may have an inner diameter that is equal to or lower than an outer diameter of the distal tip 102.

As visible on FIG. 7, the medical container 100 may comprise a cap 106 having an external thread 108 configured to engage the internal thread 60 of the adaptor 1 so as to secure the cap to the adaptor 1. The cap 106 is configured to be secured to the adaptor 1 without its external thread abutting against the gripping member 50, more specifically the free distal lip 52 of the gripping member 50. Therefore, the cap 106 may include a connecting portion whose length is lower than a distance between the distal end of the adaptor 1 and the gripping member 50. The connecting portion extends from a proximal abutment surface 110 configured to abut against the distal end of the adaptor 1 to the distal end of the cap external thread 108. The cap 106 may include an inner cap 112, which may be made of a softer material than the cap 106, so as to sealingly close the distal tip 102.

The disclosure also relates to a method for manufacturing the above-described adaptor 1. This method may include overmolding or co-injection molding of the gripping member 50 with the rest of the adaptor 1. Preferably, the adaptor 1 is formed in a two-shot injection molding process.

The invention claimed is:

1. A medical container comprising:

a distal tip; and an adaptor, said adaptor comprising:

a distal part configured to receive a connector, and a proximal part configured to be mounted onto the distal tip of the medical container, wherein the proximal part comprises an inner ring protruding from a lateral tubular wall of the adaptor, said inner ring having an inner edge that delimits an opening configured to receive the distal tip, and wherein the proximal part further comprises at least one gripping member made of an elastomer material, said at least one gripping member being connected to the inner edge of the inner ring in order to be in contact with an outer surface of the distal tip when the adaptor is mounted onto the medical container, wherein the inner ring comprises a protrusion or a recess that engages a complementarily shaped recess or protrusion provided on the at least one gripping member in order to secure said at least one gripping member to the inner ring, wherein the at least one gripping member comprises several gripping members, each of said gripping members being in the form of a partial sleeve, adjacent ones of said gripping members thereby delimiting gaps and allowing the inner edge of the inner ring to be in contact with the outer surface of the distal tip when the adaptor is mounted onto the medical container, and wherein the distal tip comprises a plurality of radial bumps extending outward from the outer surface of the distal tip and all radial bumps of said plurality of radial bumps are received in the gaps delimited by said adjacent ones of said gripping members, and wherein the plurality of radial bumps contact the inner edge of the inner ring within the gaps.

2. The medical container according to claim 1, wherein the inner ring comprises a distal abutment surface and a proximal abutment surface abutting against the at least one gripping member in order to secure said at least one gripping member in a longitudinal direction of the adaptor.

3. The medical container according to claim 1, wherein said protrusion or said recess of said inner ring or said complimentarily shaped recess or protrusion of the at least one gripping member has a dovetail shape in a cross-sectional view taken along a plane extending through a central longitudinal axis of the adaptor.

4. The medical container according to claim 1, wherein the at least one gripping member comprises a free distal lip.

5. The medical container according to claim 1, wherein the at least one gripping member is over-molded or co-injection molded.

6. The medical container according to claim 1, wherein the elastomer material of the at least one gripping member is rubber or thermoplastic elastomer.

7. A method for manufacturing the adaptor of the medical container according to claim 1, wherein the at least one gripping member is overmolded or co-injection molded.

8. The method according to claim 7, wherein the adaptor is formed by two-shot injection molding.

* * * * *